US012408992B2

(12) United States Patent
Birenbaum et al.

(10) Patent No.: US 12,408,992 B2
(45) Date of Patent: Sep. 9, 2025

(54) VOLUMETRIC FILTER OF FLUOROSCOPIC SWEEP VIDEO

(71) Applicant: Covidien LP, Mansfield, MA (US)

(72) Inventors: Ariel Birenbaum, Raanana (IL); Shaked Pessah, Maccabim-Reut (IL); Guy Alexandroni, Yehud-Monosson (IL)

(73) Assignee: Covidien LP, Mansfield, MA (US)

( * ) Notice: Subject to any disclaimer, the term of this patent is extended or adjusted under 35 U.S.C. 154(b) by 3 days.

(21) Appl. No.: 18/288,355

(22) PCT Filed: May 19, 2022

(86) PCT No.: PCT/IB2022/054648
§ 371 (c)(1),
(2) Date: Oct. 25, 2023

(87) PCT Pub. No.: WO2022/248982
PCT Pub. Date: Dec. 1, 2022

(65) Prior Publication Data
US 2024/0206980 A1   Jun. 27, 2024

Related U.S. Application Data

(60) Provisional application No. 63/192,873, filed on May 25, 2021.

(51) Int. Cl.
*A61B 34/20* (2016.01)
*A61B 6/00* (2024.01)
(Continued)

(52) U.S. Cl.
CPC .............. *A61B 34/20* (2016.02); *A61B 6/12* (2013.01); *A61B 6/4441* (2013.01); *A61B 6/487* (2013.01);
(Continued)

(58) Field of Classification Search
CPC ......... A61B 6/12; A61B 6/4441; A61B 6/487; A61B 6/5258; A61B 34/20;
(Continued)

(56) References Cited

U.S. PATENT DOCUMENTS

2014/0321710 A1   10/2014   Robert et al.
2021/0319616 A1*  10/2021   Sabczynski ............ G06T 15/08

FOREIGN PATENT DOCUMENTS

EP   3618005 A1   3/2020

OTHER PUBLICATIONS

PCT Search Report and Written Opinion issued in PCT Application No. PCT/IB2022/054648 dated Sep. 26, 2022.

* cited by examiner

*Primary Examiner* — Chao Sheng
(74) *Attorney, Agent, or Firm* — Weber Rosselli & Cannon LLP

(57) ABSTRACT

Object detection including receiving a fluoroscopic video including a plurality of fluoroscopic images captured by a fluoroscope rotated about a patient, generating a three-dimensional (3D) volumetric reconstruction from the fluoroscopic images, deleting values in the 3D volumetric reconstruction beyond a region of interest about an object, generating 2D images from a remaining 3D volumetric reconstruction following the deleting of values: detecting the object in the 2D images to determine an initial position of the object, and refining the detected initial position of the object.

20 Claims, 9 Drawing Sheets

(51) Int. Cl.
*A61B 6/12* (2006.01)
*G06T 7/70* (2017.01)
*G06T 15/08* (2011.01)
*A61B 90/00* (2016.01)

(52) U.S. Cl.
CPC .............. *A61B 6/5258* (2013.01); *G06T 7/70* (2017.01); *G06T 15/08* (2013.01); *A61B 2034/2051* (2016.02); *A61B 2090/376* (2016.02); *G06T 2207/10016* (2013.01); *G06T 2207/10064* (2013.01); *G06T 2210/41* (2013.01)

(58) Field of Classification Search
CPC ...... A61B 2034/2051; A61B 2090/376; G06T 7/70; G06T 2207/10016; G06T 2207/10064; G06T 2210/41; G06T 15/08
See application file for complete search history.

VOLUMETRIC FILTER OF FLUOROSCOPIC SWEEP VIDEO

BACKGROUND

Technical Field

This disclosure relates to the field fluoroscopic image processing, and particularly to systems and methods of identifying objects in fluoroscopic images.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MRI data or CT image data to generate a three-dimensional (3D) rendering, model, or volume of the particular body part such as the lungs.

The resulting volume generated from the MRI scan or CT scan is then utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

However, a 3D volume of a patient's lungs, generated from previously acquired scans, such as CT scans, may not provide a basis sufficient for accurate guiding of medical devices or instruments to a target during a navigation procedure. In some cases, the inaccuracy is caused by deformation of the patient's lungs during the procedure relative to the lungs at the time of the acquisition of the previously acquired CT data. This deformation (CT-to-Body divergence) may be caused by many different factors including, for example, changes in the body when transitioning from between a sedated state and a non-sedated state, the bronchoscope changing the patient's pose, the bronchoscope pushing the tissue, different lung volumes (e.g., the CT scans are acquired during inhale while navigation is performed during breathing), different beds, different days, etc.

Thus, another imaging modality is needed to visualize medical devices and targets in real-time and enhance the in-vivo navigation procedure.

SUMMARY

One aspect of the disclosure is directed to a method of object detection including: receiving a fluoroscopic video including a plurality of fluoroscopic images captured by a fluoroscope rotated about a patient, generating a three-dimensional (3D) volumetric reconstruction from the fluoroscopic images, deleting values in the 3D volumetric reconstruction beyond a region of interest about an object, generating 2D images from a remaining 3D volumetric reconstruction following the deleting of values, detecting the object in the 2D images to determine an initial position of the object, and refining the detected initial position of the object. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including filtering the received fluoroscopic images before generating the 3D volumetric reconstruction. The method where refining the determined initial positions includes searching for a maximum response in the filtered fluoroscopic images around the initial position of the object. The method where the received fluoroscopic images are filtered with a hessian filter. The method further including filling gaps caused by the removal by estimating a position of the object and interpolating between nearby retained images. The method further including scoring the determined position of the object. The method further including removing any images with an extreme high or extreme low score, where an extreme high score indicates additional structure obscuring the object and an extreme low score indicates a mismarking of the object. The method further including receiving a height of the object from a memory, where the object is a test marker mounted on a jig. The method further including detecting a height of the object using an electromagnetic sensor. The method where the electromagnetic sensor is associated with a catheter in an electromagnetic navigation system. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One aspect of the disclosure is directed to a navigation system including: a transmitter mat configured to transmit an electromagnetic field. The navigation system also includes a catheter configured for navigation within a luminal network of patient, the catheter including a sensor proximate a distal tip; a computing device storing in a memory thereon an application that when executed by a processor causes the computing device to: receive a fluoroscopic video including a plurality of fluoroscopic images captured by a fluoroscope rotated about a patient. The navigation system also generates a three-dimensional (3D) volumetric reconstruction from the fluoroscopic images. The navigation system also deletes values in the 3D volumetric reconstruction beyond a region of interest about a detected position of the sensor. The navigation system also generates 2D images from a remaining 3D volumetric reconstruction following the deleting of values. The navigation system also detects the distal tip in the 2D images to determine an initial position of the distal tip. The navigation system also includes refining the detected initial position of the distal tip of the catheter. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The navigation system where the application further executes a step of filtering the received fluoroscopic images before generating the 3D volumetric reconstruction. The navigation system where the application further executes a step of scoring the detected position of the distal tip. The navigation system where the application further executes a step of removing any images with an extreme high or extreme low score. The navigation system where the application further executes a step of filling gaps caused by the removal by interpolating between nearby retained images to estimate a position of the distal tip of the catheter. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method of testing accuracy of a fluoroscopic imaging device including: receiving a fluoroscopic video including a plurality of fluoroscopic images captured by a fluoroscope rotated about a test jig including a test marker at a known height, generating a three-dimensional (3D) volumetric reconstruction from the fluoroscopic images, deleting values from the 3D volumetric reconstruction beyond a region of interest of the test marker, projecting a remaining 3D volumetric reconstruction to generate 2D images, detecting the test marker in the 2D images to determine an initial position of the test marker, and refining the detected initial position of the test marker. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further includes filtering the received fluoroscopic images before generating the 3D volumetric reconstruction. The method further includes comparing the detected test marker at its final position with a mask to generate a score. The method further includes removing any images with an extreme high or extreme low score. The method further includes filling in gaps caused by the removal by interpolating between nearby retained images to estimate a position of the test marker. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various aspects and embodiments of the disclosure are described hereinbelow with references to the drawings, wherein.

DETAILED DESCRIPTION

This application is directed to methods of object detection in fluoroscopic images. Improved object detection can be utilized in a variety of procedures, some of which are discussed in greater detail below. For example, the enhanced object detection can be utilized in a fluoroscopy accuracy test to confirm that a particular fluoroscope can be employed in a luminal network navigation system. Further, the object detection methods may be employed to automatically detect a catheter. Other implementations include detecting biopsy or other tools within a lesion allowing visualization without the need for user input. Still further, the object detection methods may be employed to enhance segmentation of a catheter, bronchoscope, or anatomical structures to provide greater clarity (less blur) in a volumetric 3D reconstruction. While the forgoing are examples for implementation of the object detection methods disclosed herein, the implementations are not so limited and other implementations may be employed without departing from the scope of the disclosure.

Figure 1:
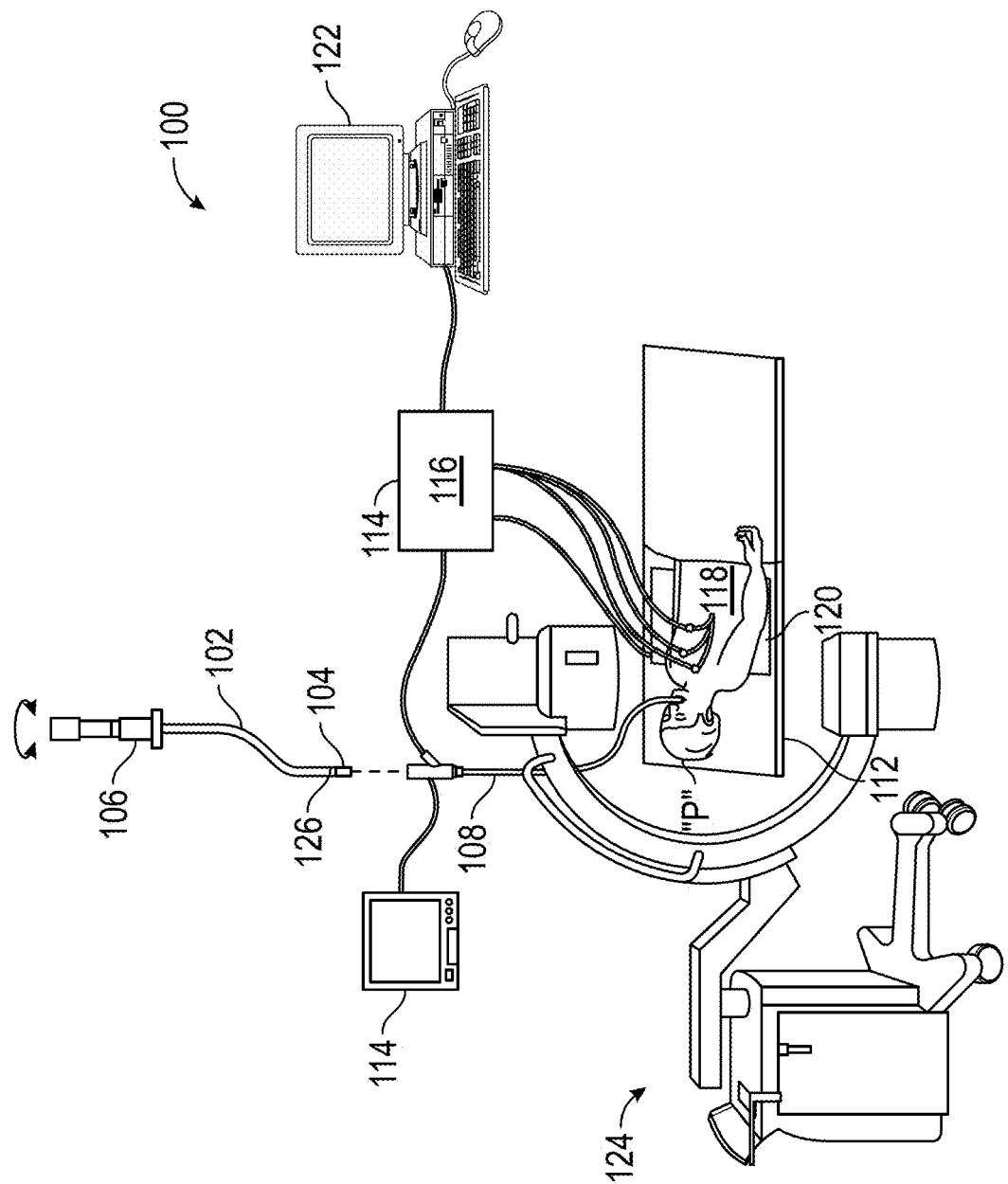
FIG. 1 is a schematic diagram of a system for navigating to soft-tissue targets via luminal networks in accordance with the disclosure.

In accordance with aspects of the disclosure, the visualization of intra-body navigation of a medical device, e.g., a biopsy tool, towards a target, e.g., a lesion, may be a portion of a larger workflow of a navigation system, such as an electromagnetic navigation system. FIG. 1 is a perspective view of an exemplary system for facilitating navigation of a medical device, e.g., a biopsy tool, to a soft-tissue target via airways of the lungs. System 100 may be further configured to construct fluoroscopic based three-dimensional volumetric data of the target area from 2D fluoroscopic images. System 100 may be further configured to facilitate approach of a medical device to the target area by using Electromagnetic Navigation Bronchoscopy (ENB) and for determining the location of a medical device with respect to the target.

One aspect of the system 100 is a software component for reviewing of computed tomography (CT) image data that has been acquired separately from system 100. The review of the CT image data allows a user to identify one or more targets, plan a pathway to an identified target (planning phase), navigate a catheter 102 to the target (navigation phase) using a user interface, and confirming placement of a sensor 104 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110, including a sensor 104 is inserted into catheter 102 and locked into position such that sensor 104 extends a desired distance beyond the distal tip of catheter 102. The position and orientation of sensor 104 relative to the reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 18 and a transmitter mat 120 including a plurality of incorporated markers (204 FIG. 2); and a computing device 122 including software and/or hardware used to facilitate identification of a target, pathway planning to the target, navigation of a medical device to the target, and/or confirmation and/or determination of placement of catheter 102, or a suitable device therethrough, relative to the target. Computing device 122 may be similar to workstation 1501 of FIG. 15 and may be configured to execute the methods of the disclosure including the method of FIGS. 10, 11, 13, and 14.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers (204 FIG. 2) incorporated with the transmitter mat 120. The markers 204 are positioned under patient P, between patient P and operating table 112 and between patient P and a radiation source or a sensing unit of fluoroscopic imaging device 124. The markers 204 incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s). One such planning software is the ILLUMISITE® planning suite currently sold by Medtronic PLC.

With respect to the navigation phase, a six degrees-of-freedom electromagnetic locating or tracking system 114, or other suitable system for determining location, is utilized for performing registration of the images and the pathway for navigation, although other configurations are also contemplated. Tracking system 114 includes the tracking module 116, a plurality of reference sensors 118, and the transmitter mat 120 (including the markers 204). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. The six degrees of freedom coordinates of reference sensors 118 are sent to computing device 122 (which includes the appropriate software) where they are used to calculate a patient coordinate frame of reference. Registration is generally performed to coordinate locations of the three-dimensional model and two-dimensional images from the planning phase, with the patient P's airways as observed through the bronchoscope 108 and allow for the navigation phase to be undertaken with precise knowledge of the location of the sensor 104, even in portions of the airway where the bronchoscope 108 cannot reach.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to EMN systems using EM sensors, the instant disclosure is not so limited and may be used in conjunction with flexible sensor, ultrasonic sensors, or without sensors. Additionally, the methods described herein may be used in conjunction with robotic systems such that robotic actuators drive the catheter 102 or bronchoscope 108 proximate the target.

Following registration of the patient P to the image data and pathway plan, a user interface is displayed in the navigation software which sets for the pathway that the clinician is to follow to reach the target. Once catheter 102 has been successfully navigated proximate the target as depicted on the user interface, the locatable guide 110 may be unlocked from catheter 102 and removed, leaving catheter 102 in place as a guide channel for guiding medical devices including without limitation, optical systems, ultrasound probes, marker placement tools, biopsy tools, ablation tools (i.e., microwave ablation devices), laser probes, cryogenic probes, sensor probes, and aspirating needles to the target. A medical device may be then inserted through catheter 102 and navigated to the target or to a specific area adjacent to the target.

Prior to inserting the medical device through the catheter 102, a local registration process may be performed for each target to reduce the CT-to-body divergence. In a capture phase of the local registration process, a sequence of fluoroscopic images may be captured and acquired via fluoroscopic imaging device 124, optionally by a user and according to directions displayed via computing device 122. A fluoroscopic 3D reconstruction may be then generated via computing device 122. The generation of the fluoroscopic 3D reconstruction is based on the sequence of fluoroscopic images and the projections of structure of markers 204 incorporated with transmitter mat 120 on the sequence of images. One or more slices of the fluoroscopic 3D reconstruction may be then displayed to the user on a display via computing device 122, optionally simultaneously. The slices of 3D reconstruction may be presented on the user interface in a scrollable format where the user is able to scroll through the slices in series.

In a marking phase of the local registration process, the clinician may be directed to identify and mark the target while using the slices of the 3D reconstruction as a reference. The user may also be directed to identify and mark the navigation catheter tip in the sequence of fluoroscopic 2D images. An offset between the location of the target and the navigation catheter tip may be then determined or calculated via computer device 122. The offset may be then utilized, via computing device 122, to correct the location and/or orientation of the navigation catheter on the display with respect to the target and/or correct the registration between the three-dimensional model and tracking system 114 in the area of the target and/or generate a local registration between the three-dimensional model and the fluoroscopic 3D reconstruction in the target area.

Figure 2:
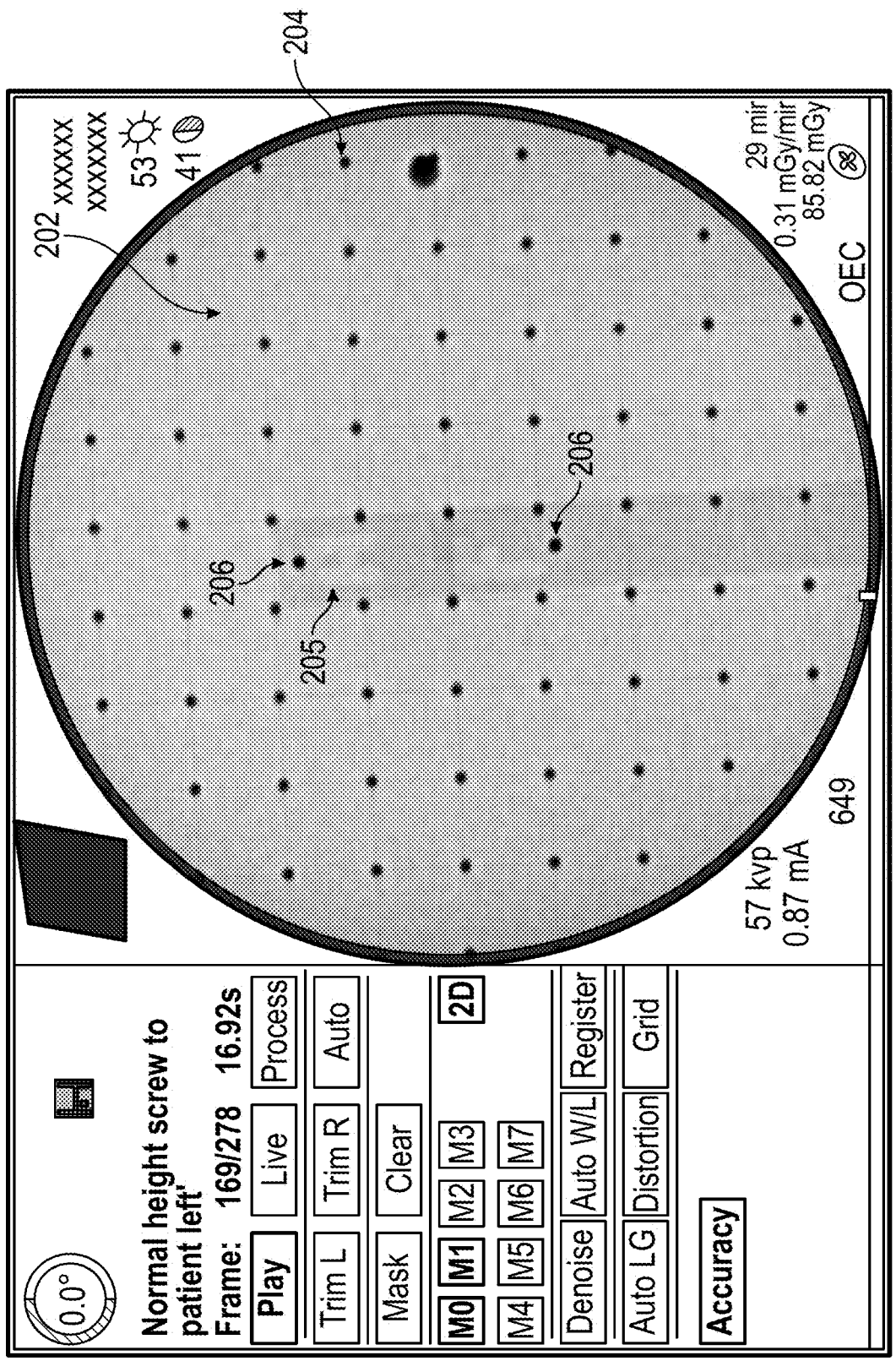
FIG. 2 is a user interface depicting a fluoroscopic image of a jig including a pair of test markers in accordance with the disclosure.

One aspect of the disclosure is directed at a method of assessing fluoroscope 124 for use in system 100, as described herein above. Not every brand of fluoroscope can be so employed, and it is important that before being placed into service that even those brands of fluoroscope that can be used with system 100, that an accuracy test is undertaken. With reference to FIG. 2, a fluoroscopic image 202 is depicted showing a pattern of spherical markers 204, which as noted above can be embedded in the transmitter mat 120. In one aspect of the disclosure, the accuracy test is performed using a generally translucent plastic jig 205 as depicted in FIG. 2 on which two test markers 206 are secured at a known height. The fluoroscopic image 202 is just a single image from a fluoroscopic video captured by a fluoroscope 124 as it is swept through an angle of between 30 and 180 degrees about the patient, generally between 30 and 50 degrees. Generally, the sweep of the fluoroscope is centered on the AP position and for example extends from about 20 degrees on one side of the AP position to about 20 degrees on the other side of the AP position.

Traditionally, when setting up a system 100 for use, an accuracy test must be performed on the fluoroscope 124. This accuracy test involves the manual marking of the location of an object in a number of frames from a fluoroscopic sweep.

Figure 5:
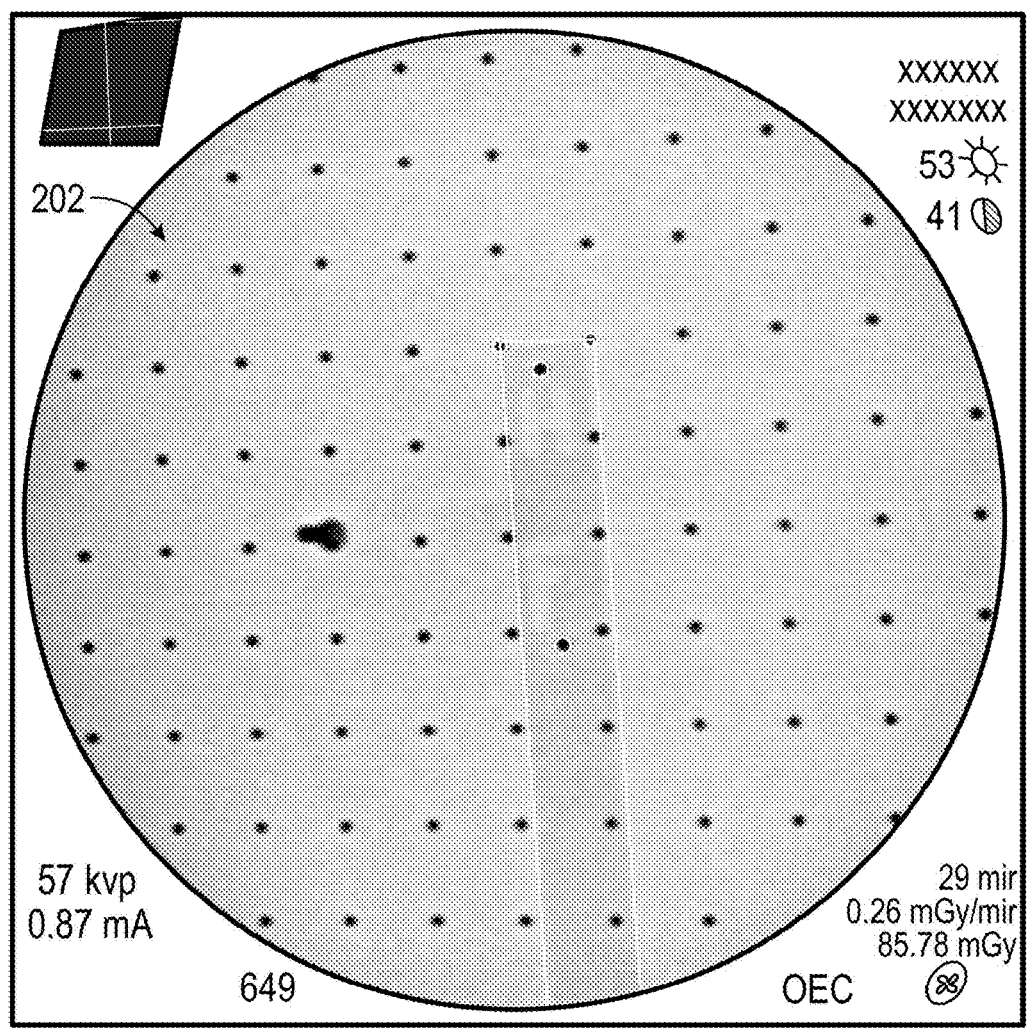
FIG. 5 depicts a fluoroscopic image in accordance with the disclosure.
Figure 6:
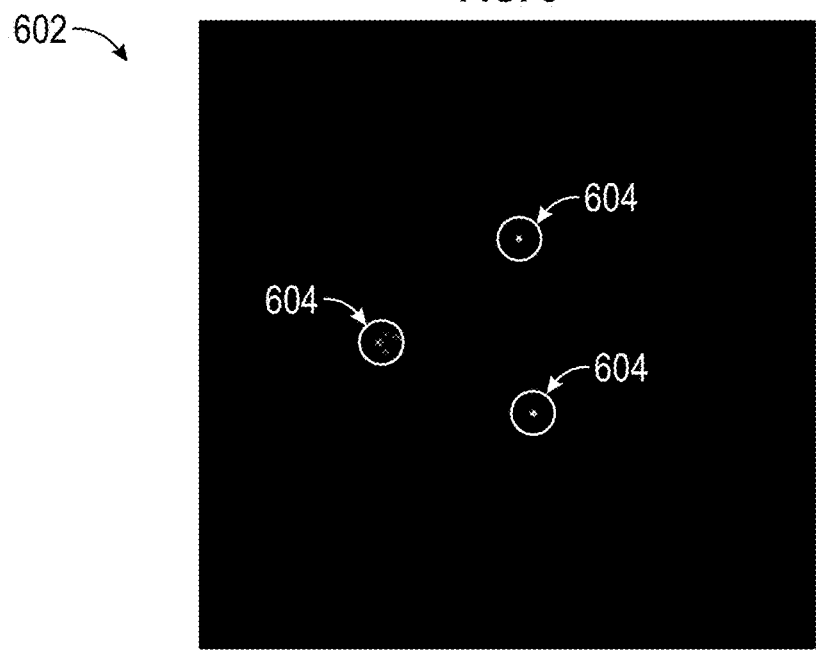
FIG. 6 depicts the results of a Hessian filter applied to the image of FIG. 5.
Figure 7:
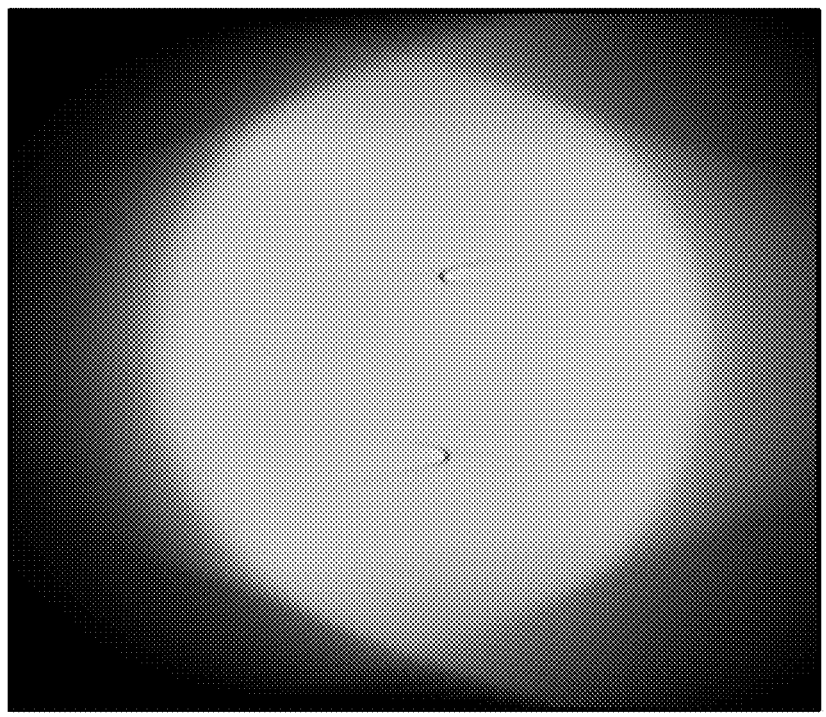
FIG. 7 depicts a three-dimensional volumetric reconstruction generated from a sweep of a fluoroscopic imaging device.
Figure 8:
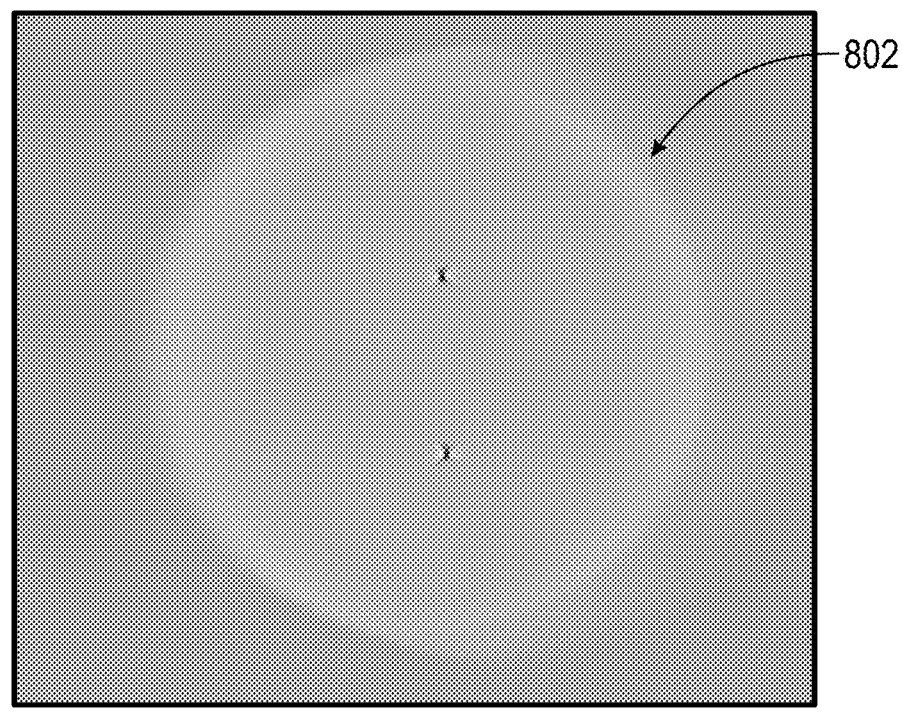
FIG. 8 depicts a three-dimensional volumetric reconstruction generated from a sweep of a fluoroscopic imaging device.
Figure 9:
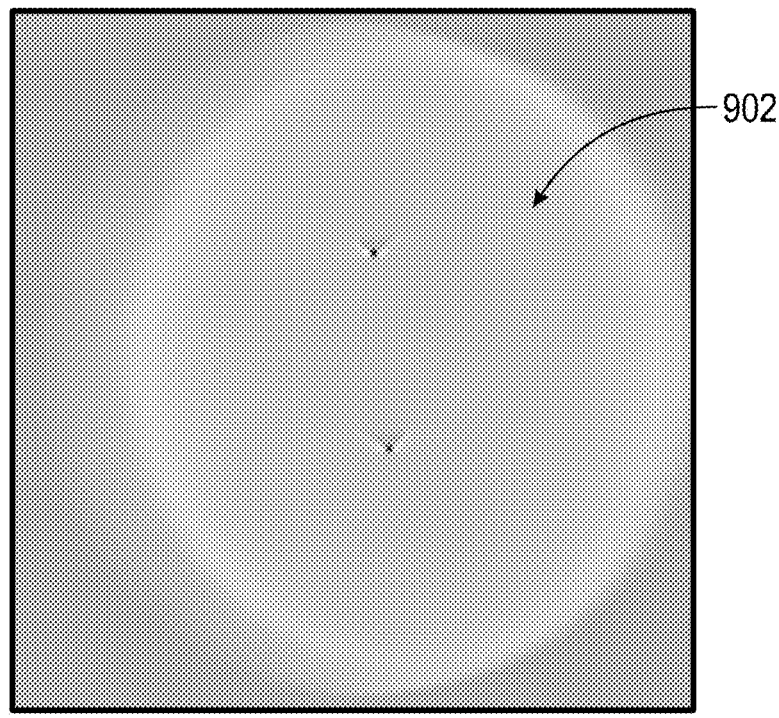
FIG. 9 depicts a 2D projection of the 3D volumetric reconstruction of FIG. 8.
Figure 10:
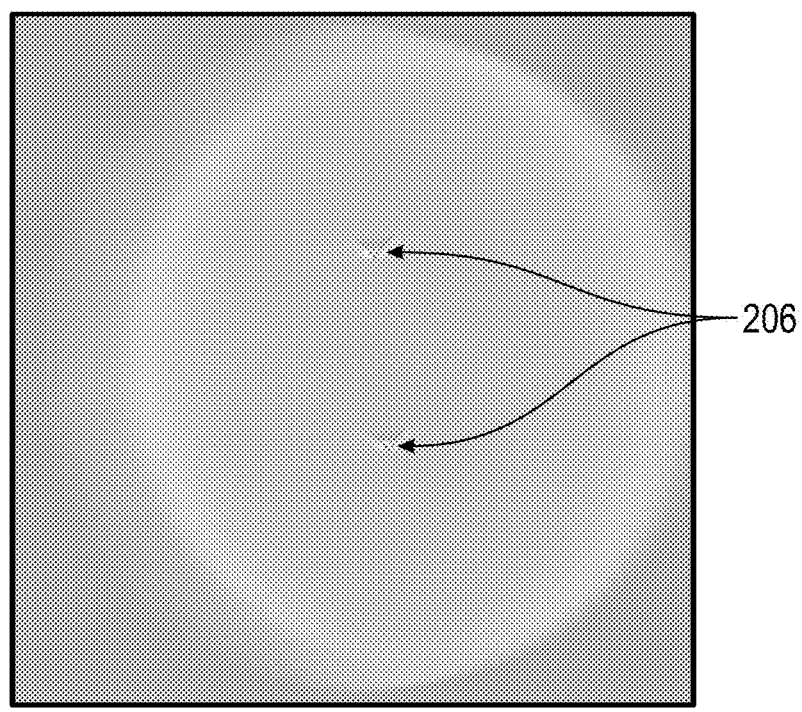
FIG. 10 depicts the initial determination of the location of the test markers.
Figure 11:
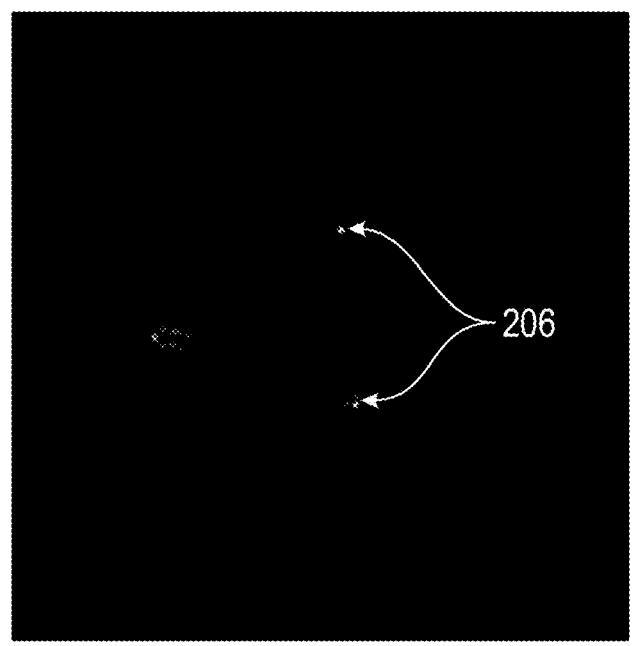
FIG. 11 depicts a Hessian filtered image for refining the initial test marker location of FIG. 10.

A method of automatically testing the accuracy of a fluoroscope 124 is described with reference to FIG. 3 and method 300 described therein. The method 300 may be embodied in an application stored in a memory associated with the computing device 122 and executed by a processor operably associated with the computer. The method 300 starts with the capture of fluoroscopic images (e.g., a fluoroscopic video) to produce a number of images 202, FIG. 5. In accordance with the disclosure, these acquired fluoroscopic images 202 may optionally be filtered at step 304 using, for example, a Hessian filter or another filtering method known to those of skill in the art including for example neural networks trained for object detection and segmentation, to produce the image 602 in FIG. 6, whereby the white dots 604 represent the test markers 206. The filtering with, for example a Hessian filter, is used here to identify structures with dimensions similar to the test markers 206. The filtered images 602 may be employed later in the process to refine marker detection. Regardless of whether the images 202 are filtered, a 3D volumetric reconstruction is generated at step 306. FIGS. 7 and 8 depict slice images from a 3D volumetric reconstruction. At step 308, a height of the test markers 206 is recalled the memory in the computing device 122. Because the height of the test markers 206 is known, at step 310 any values in the 3D volumetric reconstruction outside of a range around the known height (e.g., beyond a region of interest, such as that containing an object of interest) can be deleted from the volumetric reconstruction. For example, any slices of the 3D volumetric reconstruction that are outside of a range from the known height of the test marker 206 can be removed from the 3D volumetric reconstruction, resulting in a much smaller volume. After removal of the values or slices outside the range at the known height of the test markers 206, at step 312 the remaining volume 802 in FIG. 8 is projected to generate 2D images 902 in FIG. 9. At step 314 the locations of the test markers 206 are detected. Detection may be undertaken via any method of object detection including for example maximum value identification in the projected image 902. Because the projected images are limited to a region of interest about the test markers, the projected images should have very little if any structures obstructing or creating interference with the test markers 206, FIG. 10 and false detections such as the third detection seen in FIG. 6 are eliminated. Detection of the test markers 206 provides an initial estimate of the location of the markers. At step 316 the locations of the markers are refined by searching for a local-maxima in the filtered images from step 304 around the initial estimate from step 314. Thus, while FIG. 6 shows 3 potential test markers 206, by limiting the portions of the fluoroscopic images to a region of interest about the test markers 206 and searching for the local-maxima in the region of interest only two test markers 206 are depicted in FIG. 11. The local maxima of the test markers 206 in FIG. 11 is therefore a refined location of the test markers 206.

In practice, FIGS. 6 and 11 are identical Hessian filtered frames. The difference is achieved by limiting the volume for projecting the image of FIG. 10 to a region of interest at the test markers 206 height. Thus FIG. 10 acts as an initial guess as to the location of the test markers. The initial guess for the location of the test markers 206 is then refined by analyzing a small bounding box around the initial guesses the guesses are confirmed as shown in FIG. 11.

Figure 12:
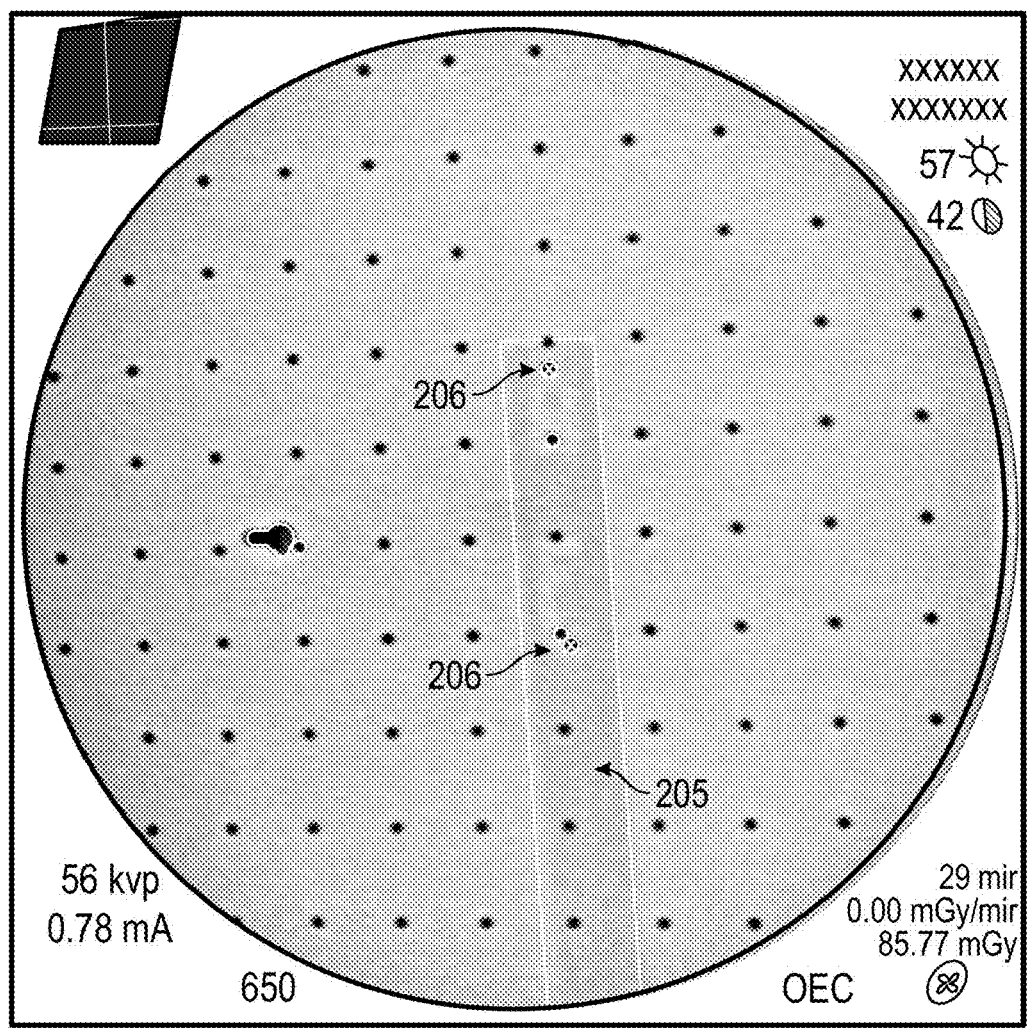
FIG. 12 depicts the detection of the location of the test markers in the fluoroscopic images.

FIG. 12 depicts the result of the test maker 206 detection process, and visual confirmation of the detected position of the test markers 206 corresponds with the physical location of the test markers 206 in the image. In FIG. 12, the refined positions of the test markers 206 is overlaid on the original image showing that the detected locations are in fact on the test markers 206.

Figure 4:
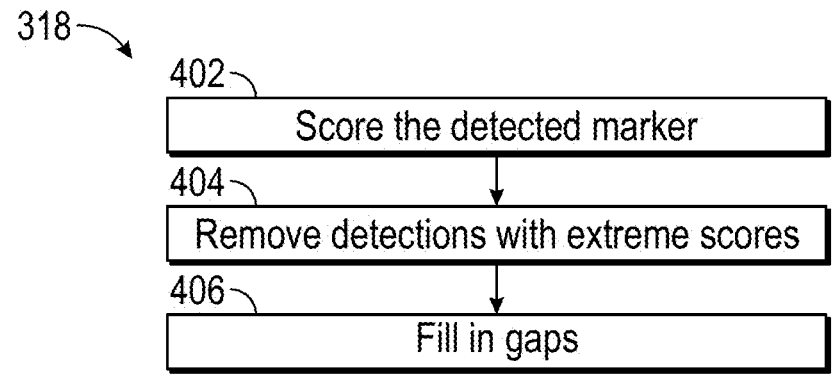
FIG. 4 is a flow chart depicting a method of post processing in accordance with the disclosure.
Figure 13D:
FIGS. 13A-13D depict a comparison of a mask, and actual mark, an obstruction, and a mismarking of the test markers.
Figure 13C:
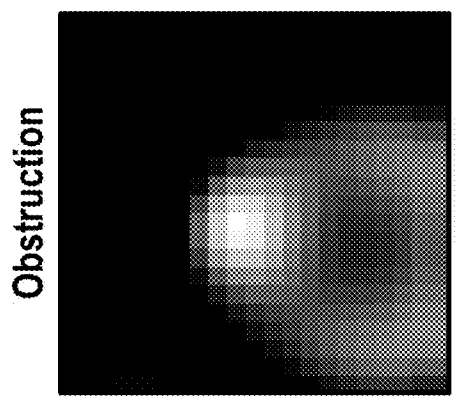
Figure 13B:
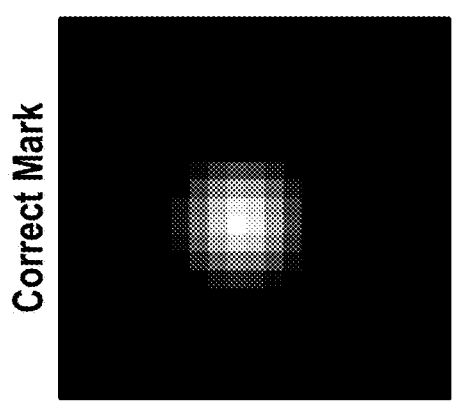
Figure 13A:
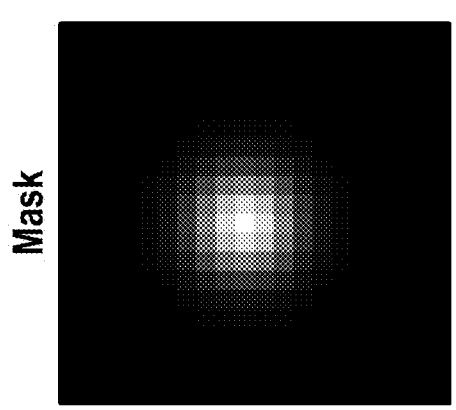
Figure 14:
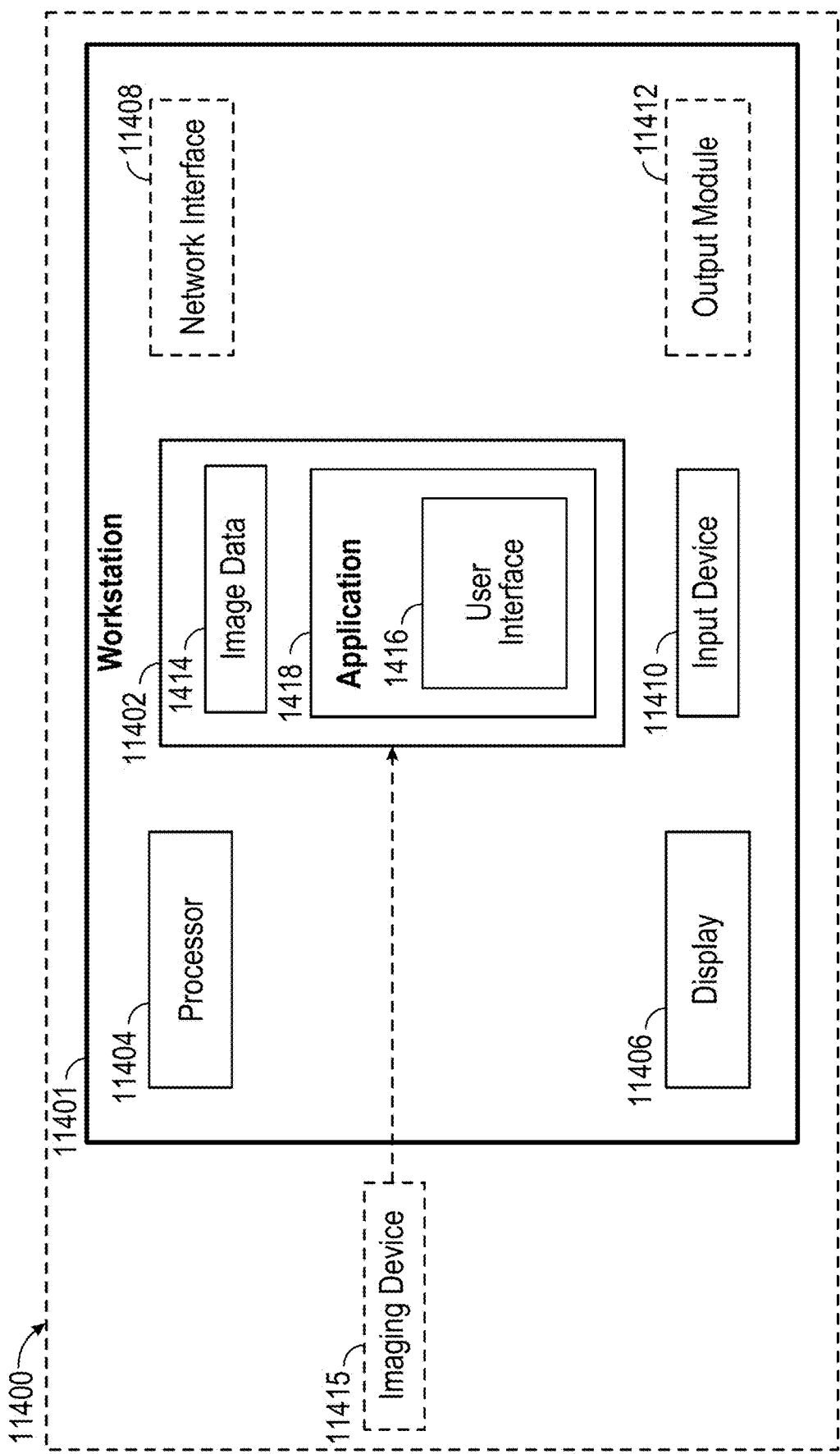
FIG. 14 is a schematic image of a system for execution of the applications, software, and methods of the disclosure.

Post processing of the projected and filtered images can be undertaken at step 318 to further confirm that the detected locations are accurate. FIG. 4 describes one example of post processing steps in accordance with the disclosure. The images of the detected test marker 206 may be given a "sphere score," at step 402. In one example, the score may be determined by comparing the image of the test marker 206 (FIG. 13B) to a mask (FIG. 13A). If there is general correspondence, then the application determines that the image of the test marker 206 is accurate. Where there are detections with an extreme high or low score, these images are removed at step 404. For example, if there are in an excess number of pixels if the image (FIG. 13C) of the test mark 206 that show structure beyond the mask then the detected test mark 206 has an extremely high score and may be rejected as it includes structure beyond the expected size of the test marker 206. Similarly, if the image contains no pixels showing structure (FIG. 13D), then the image may have an extremely low score and again be rejected e.g., as a mismark. At step 406, gaps in the detection of the test mark 206 can be filled in by interpolating between the neighboring images in which the test marker 206 is accurately detected.

Though described above in connection with using a mask, the instant disclosure is not so limited with respect to scoring. Alternatively, scoring may be undertaken by other mechanisms such as a detection score output by a neural network. As an example, the filtering operation may be performed by a neural network outputting an object segmentation probability for each image. The detection score is based on the segmentation probability.

In this manner, a fluoroscope's accuracy can be assessed for example during the set-up of the navigation system 100. If the test marks 206 are accurately detected, then the fluoroscope 124 may be confirmed as useable with the navigation system 100. These post processing steps may be undertaken prior to presentation of the result of the accuracy test as shown in FIG. 12.

Though described in connection with a fluoroscope accuracy test, the disclosure is not so limited. For example, the same or similar processes may be undertaken to identify the location of the distal tip of the catheter during a local registration process. As noted above, a central aspect of the volumetric filtering process described in connection with the fluoroscope accuracy test is the use of the height of the object being detected. When navigating a catheter 102 to a location within a patient, a sensor 104 or 126 tracks the location of the distal tip of the catheter 102 as it is navigated through the luminal network. That position of the sensor 104 or 126 is in relation to an electromagnetic (EM) field generated by the transmitter mat 120. Accordingly, at any time the sensor 104 or 126 is in the EM field the height of the catheter tip can be accurately determined.

Figure 3:
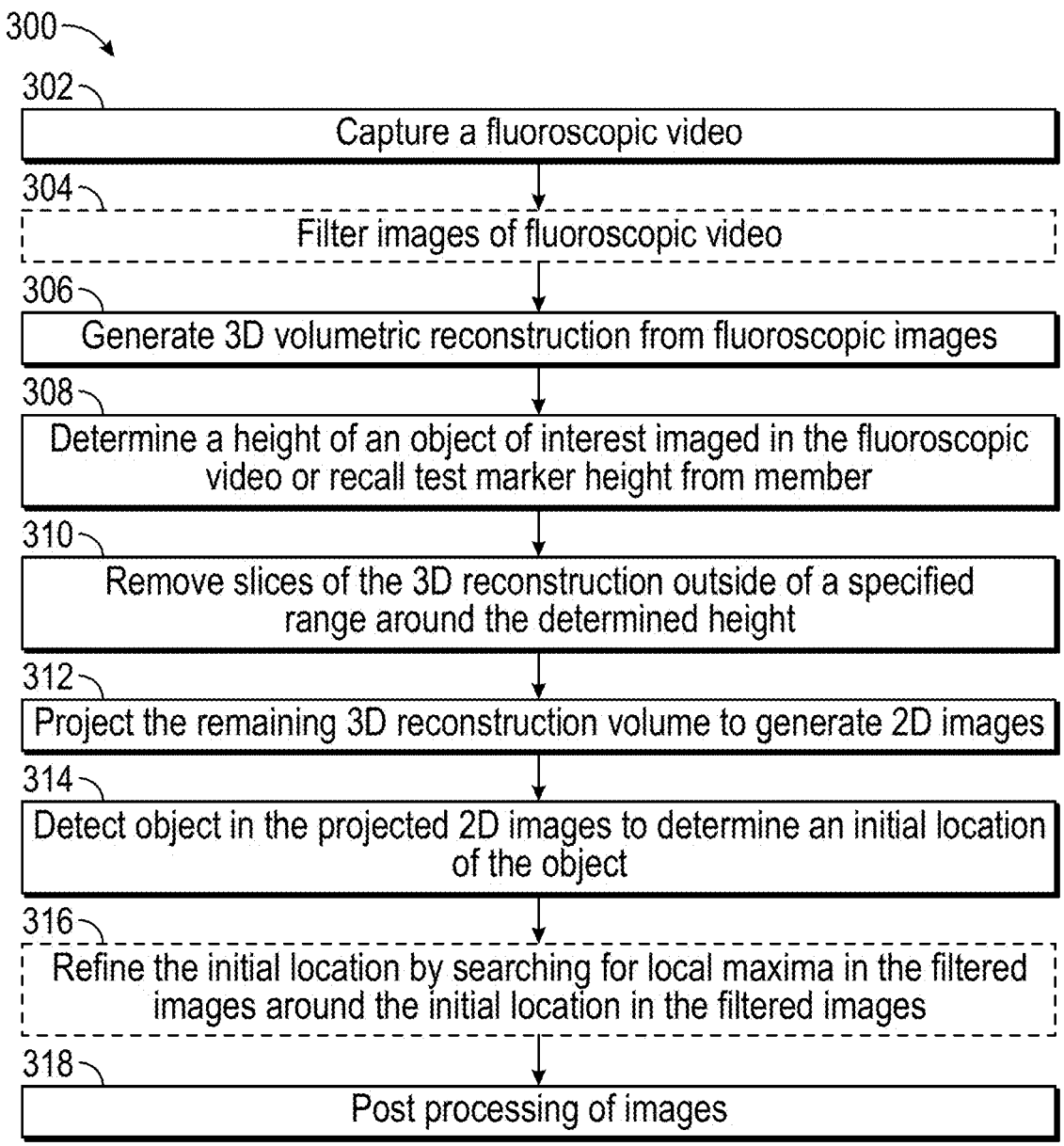
FIG. 3 is a flow chart depicting a method of detecting an object in a fluoroscopic image in accordance with the disclosure.

Accordingly, when conducting a local registration, rather than requiring the user to mark the location of catheter tip in two slices from the entirety of the 3D volumetric reconstruction, the process of FIG. 3 can be employed to limit 3D volumetric reconstruction to those slices within some range around the location of the target. As will be recognized, unlike in the fluoroscope accuracy test, the position of the distal tip of the catheter is not static, but rather moves within some range due to either breathing or the heat beat of the patient. Typically, the local registration is performed under breath hold conditions and during a period where the lungs have essentially equalized the pressure and have substantially stopped movement caused by breathing. This still leaves movement caused by the heartbeat, but this movement is relatively small by comparison, and while it may increase the range around the height of the tip of the catheter 102 for which slices of the 3D reconstruction are retained. The remaining steps of the method 300 and 400 may be employed to automatically detect the location of the distal tip of the catheter in the 3D volumetric reconstruction, thus automating at least one of the processes of the local registration process.

Another aspect of the disclosure is that the distal tip of the catheter 102 can be tracked throughout the fluoroscopic sweep in instances where a breath hold is not undertaken or where there is high wig-wag (rotation about a third plane of axis of the fluoroscope) in the fluoroscopic sweep. Tracking the tip of the catheter 102 improves the quality of the 3D reconstruction enabling visualization of the target. During breathing the detected catheter position can be used to modify the fluoroscopic pose to ensure that in the reconstructed volume the target (or the end of the catheter are always rendered sharply or crisply while the background is rendered blurry, which further improves the clarity of target or catheter. Similarly, during wigwag the catheter tip position can be used to more accurately solve for the pose of the fluoroscope, and again improve image quality. Thus, better tracking achieves better accuracy in the calculations for visualization and registration (local registration).

Yet a further aspect of the disclosure is directed the detection of biopsy and therapy tools and particularly detection of those devices in a lesion. Where the user has reasonable belief that the biopsy or therapy tool has been inserted into a lesion or tumor, a fluoroscopic sweep is often acquired to confirm placement. The height of the tool from the transmitter mat 120 is known from the detected height of the sensor 104 or 126 in the catheter 102 or where appropriate a similar sensor located in the tool itself. Using that height and following acquisition of images from a fluoroscopic sweep and generation of a 3D volumetric reconstruction, the slices of the 3D reconstruction outside of a range around the height of the tool. The tool (either biopsy or therapy) has a known profile. These profiles can be detected in the projected images of the 3D reconstruction, similar to the spheres described above for the fluoroscope accuracy test. Other steps of the process described in method 300 and 400 may also be employed to complete the detection process. Further, because of the narrowing of the images to be processed is reduced, additional image processing can be employed to automatically detect the boundaries of the tumor or lesions. As a result, confirmation of the presence of the tool in the lesion for therapy or biopsy can be automatically confirmed and an indicator presented to the user on a user interface regarding the placement. Other details about the placement may also be presented such as proximity to a center of the lesion, distances from boundaries, etc.

Still further, the processes described herein can be employed in the segmentation of objects such as the catheter, bronchoscope or other anatomical structures such as the ribs. For example, by selecting a sub-range of height (e.g., a sub range of slices) for processing, obscured portions of the patient can be selectively removed from the 3D volumetric reconstruction. Segmentation algorithms are known to yield false positives in fluoroscopic images. Utilizing the processes described herein, the portions of the 3D volumetric reconstruction at heights outside of the range of range of heights around the height of the object or target being imaged are deleted. As a result, any false positives at these undesired heights can be filtered out of any projected image. Any false positives that might be generated using a metal removal segmentation mask, that might otherwise cause degraded results, can thus be further enhanced by this process. For example, the heart may obscure the ribs. A volumetric reconstruction may be generated from the fluoroscopic sweep. The portions of the reconstruction containing the obstruction can be deleted from the 3D volumetric reconstruction. The remaining volumetric reconstruction can then be projected and the desired object (e.g., the ribs that are obscured) can be segmented on those projections. In some instances, where for example organs are concerned it may be necessary to delete an amorphic shape in the 3D volume and not individual slices.

Additionally, or alternatively, visualization may be enhanced using for example metal removal algorithms or auto-window level algorithms.

Reference is now made to FIG. 1, which is a schematic diagram of a system 1400 configured for use with the methods of the disclosure including the method of FIGS. 3 and 4. System 1400 may include a workstation 1401, and optionally a fluoroscopic imaging device or fluoroscope 1415. In some embodiments, workstation 1401 may be coupled with fluoroscope 1415, directly or indirectly, e.g., by wireless communication. Workstation 401 may include a memory 1402, a processor 1404, a display 1406 and an input device 1410. Processor or hardware processor 1404 may include one or more hardware processors. Workstation 1401 may optionally include an output module 1412 and a network interface 1408. Memory 1402 may store an application 1418 and image data 1414. Application 1418 may include instructions executable by processor 1404 for executing the methods of the disclosure including the method of FIG. 14.

Application 1418 may further include a user interface 1416. Image data 1414 may include the CT scans, the generated fluoroscopic 3D reconstructions of the target area and/or any other fluoroscopic image data and/or the generated one or more slices of the 3D reconstruction. Processor 1404 may be coupled with memory 1402, display 1406, input device 1410, output module 1412, network interface 1408 and fluoroscope 1415. Workstation 1401 may be a stationary computing device, such as a personal computer, or a portable computing device such as a tablet computer. Workstation 1401 may embed a plurality of computer devices.

Memory 1402 may include any non-transitory computer-readable storage media for storing data and/or software including instructions that are executable by processor 1404 and which control the operation of workstation 1401 and, in some embodiments, may also control the operation of fluoroscope 1415. Fluoroscope 1415 may be used to capture a sequence of fluoroscopic images based on which the fluoroscopic 3D reconstruction is generated and to capture a live 2D fluoroscopic view according to this disclosure. In an embodiment, memory 1402 may include one or more storage devices such as solid-state storage devices, e.g., flash memory chips. Alternatively, or in addition to the one or more solid-state storage devices, memory 1402 may include one or more mass storage devices connected to the processor 1404 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1404. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1401.

Application 1418 may, when executed by processor 1404, cause display 1406 to present user interface 1416. User interface 1416 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view. User interface 1416 may be further configured to display the target mark in different colors depending on whether the medical device tip is aligned with the target in three dimensions.

Network interface 1408 may be configured to connect to a network such as a local area network (LAN) consisting of a wired network and/or a wireless network, a wide area network (WAN), a wireless mobile network, a Bluetooth network, and/or the Internet. Network interface 1408 may be used to connect between workstation 1401 and fluoroscope 1415. Network interface 1408 may be also used to receive image data 1414. Input device 1410 may be any device by which a user may interact with workstation 1401, such as, for example, a mouse, keyboard, foot pedal, touch screen, and/or voice interface. Output module 1412 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A method of object detection comprising:
receiving a fluoroscopic video including a plurality of fluoroscopic images captured by a fluoroscope rotated about a patient;
generating a three-dimensional (3D) volumetric reconstruction from the received plurality of fluoroscopic images
deleting values in the 3D volumetric reconstruction beyond a region of interest about an object;
generating 2D images from a remaining 3D volumetric reconstruction following the deleting of values;
detecting the object in the 2D images to determine an initial position of the object; and
refining the detected initial position of the object.

2. The method of claim 1, further comprising receiving a height of the object from a memory, wherein the object is a test marker mounted on a jig.

3. The method of claim 1, further comprising filtering the received plurality of fluoroscopic images before generating the 3D volumetric reconstruction.

4. The method of claim 3, wherein refining the determined initial positions comprises searching for a maximum response in the filtered plurality of fluoroscopic images around the initial position of the object.

5. The method of claim 4, wherein the received plurality of fluoroscopic images are filtered with a Hessian filter.

6. The method of claim 1, further comprising scoring the determined initial position of the object.

7. The method of claim 6, further comprising removing images from the plurality of fluoroscopic images with an extreme high or extreme low score, wherein the extreme high score indicates additional structure obscuring the object and the extreme low score indicates a mismarking of the object.

8. The method of claim 7, further comprising filling gaps caused by the removal by estimating a position of the object and interpolating image data between nearby retained images of the plurality of fluoroscopic images.

9. The method of claim 1, further comprising detecting a height of the object using an electromagnetic sensor.

10. The method of claim 9, wherein the electromagnetic sensor is associated with a catheter in an electromagnetic navigation system.

11. A navigation system comprising:
a transmitter mat configured to transmit an electromagnetic field;
a catheter configured for navigation within a luminal network of patient, the catheter including a sensor proximate a distal tip;
a computing device storing in a memory thereon an application that when executed by a processor causes the computing device to:
receive a fluoroscopic video including a plurality of fluoroscopic images captured by a fluoroscope rotated about a patient;
generate a three-dimensional (3D) volumetric reconstruction from the received plurality of fluoroscopic images;
delete values in the 3D volumetric reconstruction beyond a region of interest about a detected position of the sensor;
generate 2D images from a remaining 3D volumetric reconstruction following the deleting of values;
detect the distal tip in the 2D images to determine an initial position of the distal tip; and
refine the detected initial position of the distal tip of the catheter.

12. The navigation system of claim 11, wherein the application further executes a step of filtering the received plurality of fluoroscopic images before generating the 3D volumetric reconstruction.

13. The navigation system of claim 11, wherein the application further executes a step of scoring the determined initial position of the distal tip.

14. The navigation system of claim 13, wherein the application further executes a step of removing images from the plurality of fluoroscopic images with an extreme high or extreme low score.

15. The navigation system of claim 14, wherein the application further executes a step of filling gaps caused by the removal by interpolating image data between nearby retained images from the plurality of fluoroscopic images to estimate a position of the distal tip of the catheter.

16. A method of testing accuracy of a fluoroscopic imaging device comprising:

receiving a fluoroscopic video including a plurality of fluoroscopic images captured by a fluoroscope rotated about a test jig including a test marker at a known height;

generating a three-dimensional (3D) volumetric reconstruction from the received plurality of fluoroscopic images;

deleting values from the 3D volumetric reconstruction beyond a region of interest of the test marker;

projecting a remaining 3D volumetric reconstruction to generate 2D images;

detecting the test marker in the 2D images to determine an initial position of the test marker; and refining the determined initial position of the test marker.

17. The method of claim 16, further comprising filtering the received plurality of fluoroscopic images before generating the 3D volumetric reconstruction.

18. The method of claim 16, further comprising comparing the detected test marker at its final position with a mask to generate a score.

19. The method of claim 18, further comprising removing images from the plurality of fluoroscopic images with an extreme high or extreme low score.

20. The method of claim 19, further comprising filling in gaps caused by the removal by interpolating image data between nearby retained images from the plurality of fluoroscopic images to estimate a position of the test marker.

* * * * *